(12) United States Patent
Park

(10) Patent No.: US 10,201,328 B2
(45) Date of Patent: Feb. 12, 2019

(54) ULTRASONIC DIAGNOSTIC APPARATUS AND MANUFACTURING METHOD THEREOF

(71) Applicant: SAMSUNG MEDISON CO., LTD., Hongcheon-gun, Gangwon-do (KR)

(72) Inventor: Byung Joo Park, Gyeongsangbuk-do (KR)

(73) Assignee: SAMSUNG MEDISON CO., LTD., Hongcheon-Gun, Gangwon-do (KR)

( * ) Notice: Subject to any disclaimer, the term of this patent is extended or adjusted under 35 U.S.C. 154(b) by 1003 days.

(21) Appl. No.: 14/577,827

(22) Filed: Dec. 19, 2014

(65) Prior Publication Data

US 2015/0173714 A1 Jun. 25, 2015

(30) Foreign Application Priority Data

Dec. 20, 2013 (KR) .......... 10-2013-0159833
Aug. 5, 2014 (KR) .......... 10-2014-0100523

(51) Int. Cl.
*B06B 1/06* (2006.01)
*A61B 8/00* (2006.01)
(Continued)

(52) U.S. Cl.
CPC .......... *A61B 8/4494* (2013.01); *A61B 8/4483* (2013.01); *B06B 1/0622* (2013.01);
(Continued)

(58) Field of Classification Search
CPC ....... B06B 1/06; B06B 1/0603; B06B 1/0644; B06B 1/0688; H01L 41/047
(Continued)

(56) References Cited

U.S. PATENT DOCUMENTS 5,553,035 A 3/1996 Seyed-Bolorforosh et al.
6,396,199 B1 * 5/2002 Douglas ................ B06B 1/0622
310/334
(Continued)

FOREIGN PATENT DOCUMENTS

CN 102308375 A 1/2012
CN 103239259 A 8/2013
(Continued)

OTHER PUBLICATIONS

European Office Action issued in Application No. 14194222.7 dated Mar. 15, 2017.
(Continued)

*Primary Examiner* — Derek Rosenau
(74) *Attorney, Agent, or Firm* — Morgan, Lewis & Bockius LLP

(57) ABSTRACT

Disclosed herein are an ultrasonic diagnostic apparatus, and a manufacturing method thereof. The ultrasonic diagnostic apparatus includes: a matching layer; a flexible printed circuit board having steps at both edge portions; a piezoelectric layer disposed below the matching layer and on the flexible printed circuit board such that a first electrode and a second electrode of the piezoelectric layer, between which steps are formed and which are separated from each other by polarization areas, are respectively connected to a first electrode and a second electrode of the flexible printed circuit board; and a backing layer disposed below the piezoelectric layer.

18 Claims, 18 Drawing Sheets

(51) Int. Cl.
   *H01L 41/25* (2013.01)
   *H05K 3/30* (2006.01)

(52) U.S. Cl.
   CPC .............. *H01L 41/25* (2013.01); *H05K 3/30* (2013.01); *Y10T 29/42* (2015.01)

(58) Field of Classification Search
   USPC ........................................ 310/322, 334, 335
   See application file for complete search history.

(56) References Cited

U.S. PATENT DOCUMENTS

| 6,761,688 B1* | 7/2004 | Mohr, III ................ B06B 1/064 |
| | | 310/334 |
| 2006/0142659 A1 | 6/2006 | Okazaki et al. |
| 2008/0238262 A1 | 10/2008 | Takeuchi et al. |
| 2008/0312537 A1 | 12/2008 | Hyuga |
| 2009/0069689 A1 | 3/2009 | Isono |

FOREIGN PATENT DOCUMENTS

| EP | 0707898 A2 | 4/1996 |
| EP | 1591067 A1 | 11/2005 |

OTHER PUBLICATIONS

Extended European Search Report dated Jun. 15, 2015, issued in corresponding European Patent Application No. 14194222.7. 8 pgs.
European Communication under Rule 71(3) EPC issued in Application No. 14 194 222.7 dated Feb. 27, 2018 with text intended to grant.
Chinese Office Action issued in Application No. 201410806696.1 dated Jul. 27, 2018, with English translation.

* cited by examiner

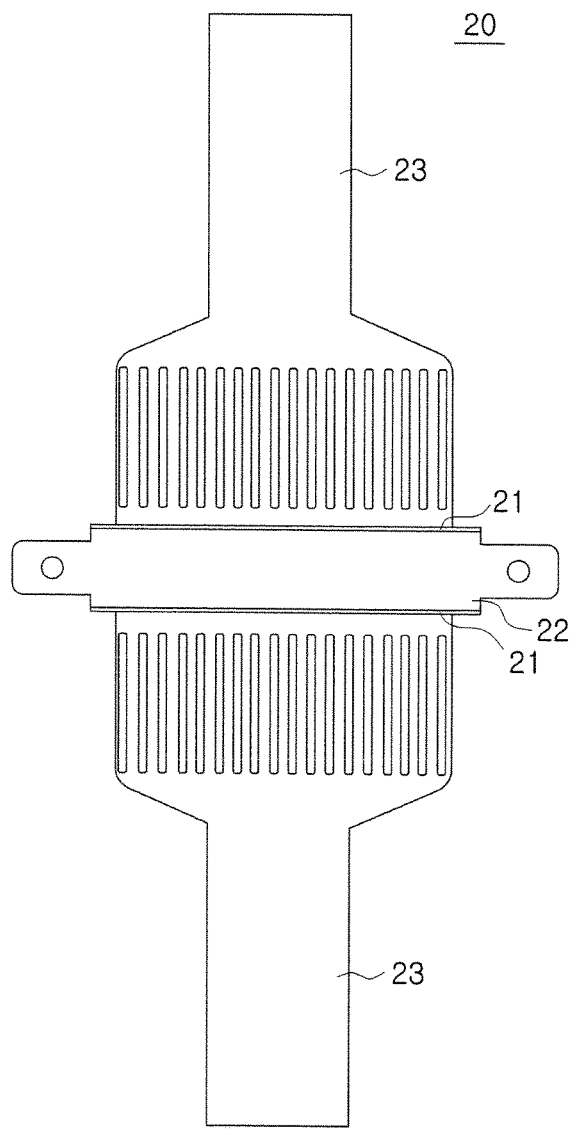

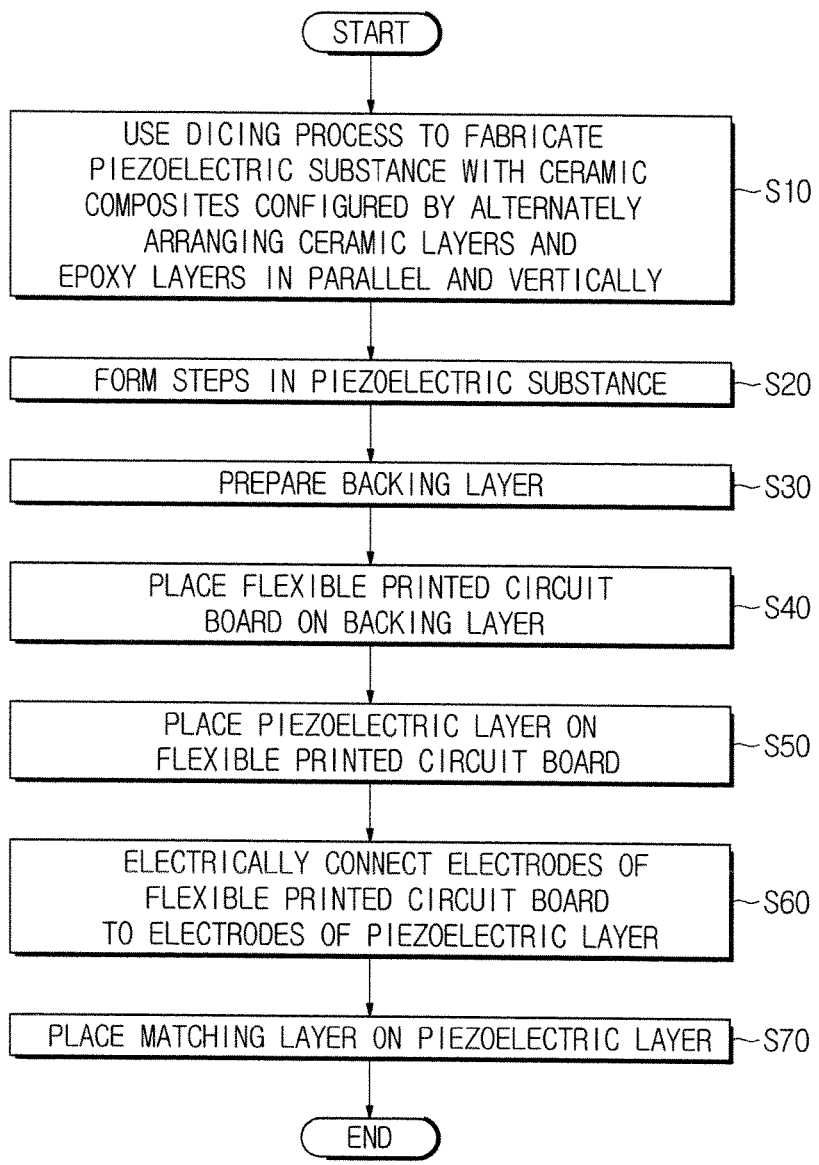

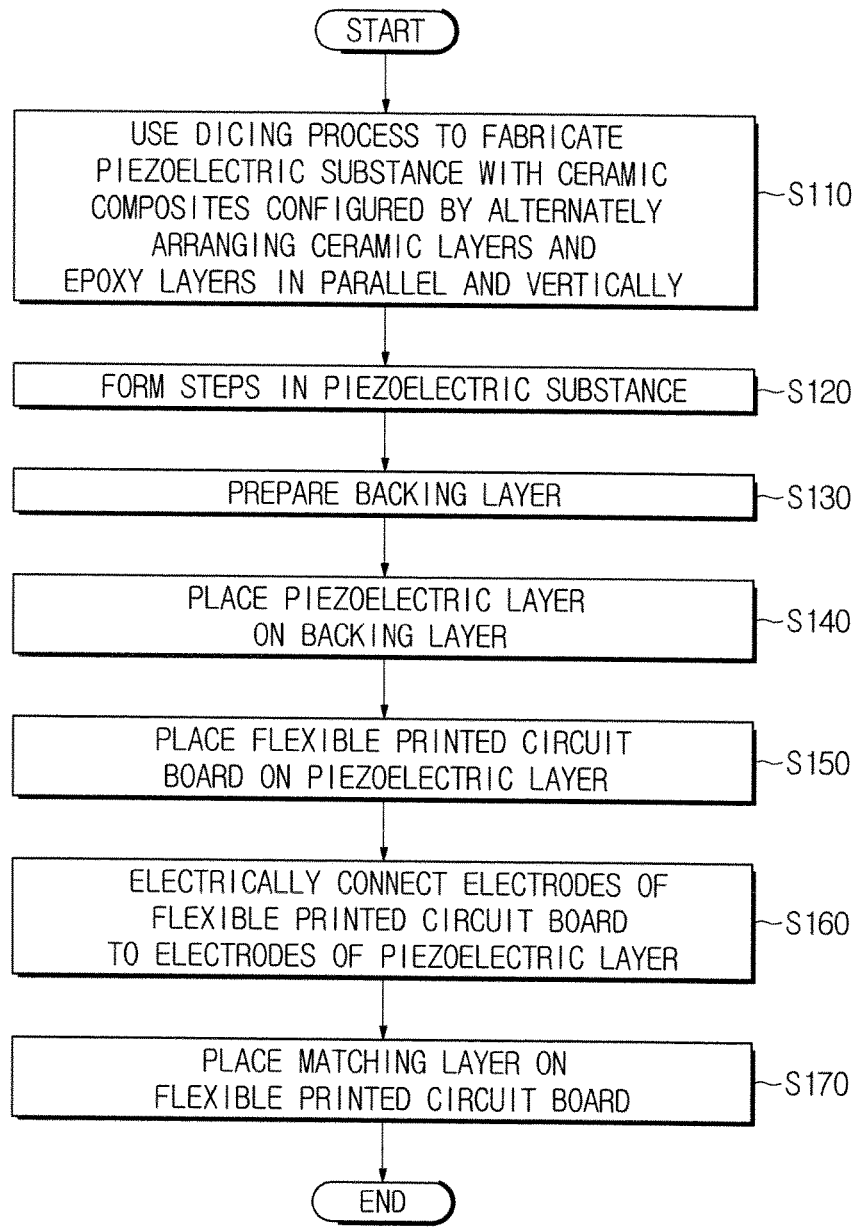

ULTRASONIC DIAGNOSTIC APPARATUS AND MANUFACTURING METHOD THEREOF

CROSS-REFERENCE TO RELATED APPLICATION

This application claims the benefit of Korean Patent Applications No. 2013-0159833, filed on Dec. 20, 2013, and No. 2014-0100523, filed on Aug. 5, 2014 in the Korean Intellectual Property Office, the disclosures of which are incorporated herein by reference.

BACKGROUND

1. Field

Embodiments of the present disclosure relate to an ultrasonic diagnostic apparatus in which steps are formed at edge portions of a piezoelectric layer to maintain the performance of the ultrasonic diagnosis apparatus while stabilizing the process of the ultrasonic diagnosis apparatus to thereby improve yield, and a manufacturing method of the ultrasonic diagnostic apparatus.

2. Description of the Related Art

An ultrasonic diagnostic apparatus irradiates ultrasonic signals to a target region of an object from the surface of the object, and receives ultrasonic signals (ultrasonic echo signals) reflected from the target region so as to non-invasively acquire section images about soft tissue of the object or images about blood vessels of the object based on information of the echo ultrasonic signals. The ultrasonic diagnostic apparatus has advantages that it is a compact, low-priced apparatus and it can display images in real time, compared to other medical imaging apparatuses, such as an X-ray diagnostic apparatus, an X-ray Computerized Tomography (CT) scanner, a Magnetic Resonance Image (MRI) apparatus, and a nuclear medical diagnostic apparatus. Also, the ultrasonic diagnostic apparatus has high safety since there is no risk for patients to be exposed to radiation such as X-rays. For the advantages, the ultrasonic diagnostic apparatus is widely used to diagnose the heart, abdomen, urinary organs, uterus, etc.

The ultrasonic diagnostic apparatus includes a transducer to transmit ultrasonic signals to an object and to receive ultrasonic echo signals reflected from the object, in order to acquire an ultrasonic image of the object.

The transducer may include a piezoelectric layer to convert electrical signals into acoustic signals or acoustic signals into electrical signals according to vibration of a piezoelectric material, a matching layer to reduce a difference in acoustic impedance between the piezoelectric layer and an object so that a major part of ultrasonic waves generated from the piezoelectric layer can be transferred to the object, a lens layer to focus ultrasonic waves moving forward from the piezoelectric layer on a specific region, and a backing layer to block ultrasonic waves from being transmitted backward from the piezoelectric layer to prevent image distortion.

SUMMARY

Therefore, it is an aspect of the present disclosure to provide an ultrasonic diagnostic apparatus in which a piezoelectric layer with steps at edge portions is electrically connected to a flexible printed circuit board, and a manufacturing method of the ultrasonic diagnostic apparatus.

Additional aspects of the disclosure will be set forth in part in the description which follows and, in part, will be obvious from the description, or may be learned by practice of the disclosure.

In accordance with one aspect of the present disclosure, an ultrasonic diagnostic apparatus includes: a matching layer; a flexible printed circuit board; a piezoelectric layer in which a first electrode and a second electrode between which steps are formed and which are separated from each other by polarization areas are respectively connected to a first electrode and a second electrode of the flexible printed circuit board, the piezoelectric layer disposed below the matching layer and on the flexible printed circuit board; and a backing layer placed below the piezoelectric layer.

The flexible printed circuit board may have steps at both edge portions, and be connected to the piezoelectric layer. Alternatively, a plurality of flexible printed circuit boards, each flexible printed circuit board having a step at one edge portion, may be connected to the piezoelectric layer.

Each step of the piezoelectric layer may correspond to a thickness of the flexible printed circuit board, and the piezoelectric layer may be configured with ceramic composites.

In accordance with one aspect of the present disclosure, a method of manufacturing an ultrasonic diagnostic apparatus, includes: providing a backing layer; placing a flexible printed circuit board on the backing layer; placing, on the flexible printed circuit board, a piezoelectric layer in which a first electrode and a second electrode between which steps are formed with respect to polarization areas are respectively connected to a first electrode and a second electrode of the flexible printed circuit board; and placing a matching layer on the piezoelectric layer.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 5 is a top view of an integrated flexible printed circuit board according to an embodiment of the present disclosure;

FIG. 10A is a flowchart illustrating a method of manufacturing an ultrasonic diagnostic apparatus, according to an embodiment of the present disclosure; and FIG. 10B is a flowchart illustrating a method of manufacturing an ultrasonic diagnostic apparatus, according to another embodiment of the present disclosure.

DETAILED DESCRIPTION

Reference will now be made in detail to the embodiments of the present disclosure, examples of which are illustrated in the accompanying drawings. In the following description, if it is determined that detailed descriptions for related art make the subject matter of the present disclosure obscure unnecessarily, the detailed descriptions will be omitted.

The following terms are terms selected in consideration of functions in the embodiments. Accordingly, the meanings of the terms may vary according to a user's or an operator's intention or judicial cases. Therefore, the meanings of the terms used in the following embodiments must be interpreted according to definitions specifically indicated in the specification. Unless specifically indicated in the specification, the terms must be interpreted as meanings generally understood in the art to which the present invention pertains.

Also, the configurations of embodiments that can be optionally or selectively implemented in the following description must be, although they are shown as a single integrated configuration in the corresponding drawings, understood to be able to be freely combined with each other, unless specifically indicated in the specification and unless the combination is determined as a technical contradiction by one of ordinary skill in the art.

Hereinafter, an ultrasonic diagnostic apparatus according to an embodiment of the present disclosure will be described with reference to the appended drawings.

Figure 1:
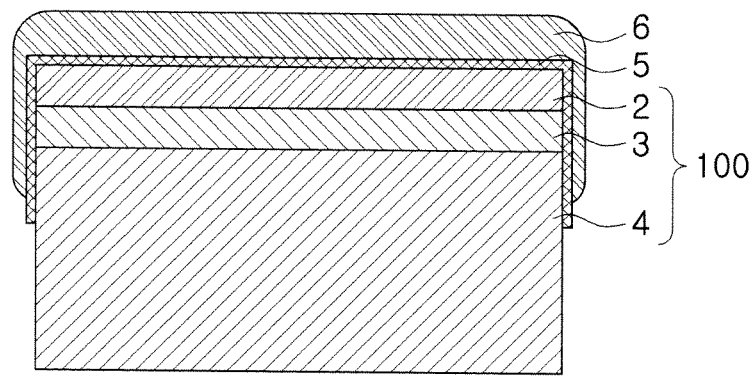
FIG. 1 is a cross-sectional view of an ultrasonic diagnostic apparatus according to an embodiment of the present disclosure.

FIG. 1 is a cross-sectional view of an ultrasonic diagnostic apparatus according to an embodiment of the present disclosure.

Referring to FIG. 1, an ultrasonic diagnostic apparatus 1 may include: an acoustic module 100 configured with a piezoelectric layer 3, a backing layer 4 disposed below the piezoelectric layer 3, and a matching layer 2 disposed on the piezoelectric layer 3; a protection layer 5 to cover the upper surface and parts of the lateral surfaces of the acoustic module 100; and a lens layer 6 to cover the upper and lateral surfaces of the protection layer 5.

The acoustic module 100 is also termed an ultrasonic transducer. The ultrasonic transducer may be a magnetostrictive ultrasound transducer using the magnetostrictive effect of a magnetic material, a capacitive micromachined ultrasonic transducer (CMUT) that transmits and receives ultrasonic waves using vibration of several hundreds or thousands of micromachined thin films, or a piezoelectric ultrasonic transducer using the piezoelectric effect of a piezoelectric material. In the current embodiment, the ultrasonic transducer is assumed to be a piezoelectric ultrasonic transducer.

An effect in which a voltage is generated when mechanical pressure is applied to a predetermined material, and an effect in which mechanical deformation occurs when a voltage is applied are called a piezoelectric effect and a converse piezoelectric effect, respectively. A material having the piezoelectric effect and the converse piezoelectric effect is called a piezoelectric material. That is, a piezoelectric material is a material of converting electricity energy into mechanical vibration energy and mechanical vibration energy into electricity energy.

The ultrasonic diagnostic apparatus 1 may include the piezoelectric layer 3 made of a piezoelectric material of converting, when an electrical signal is applied, the electrical signal into mechanical vibration to generate ultrasonic waves.

The piezoelectric material constituting the piezoelectric layer 3 may be a ceramic of lead zirconate titanate (PZT), a PZMT single crystal containing a solid solution of lead magnesium niobate and lead titanate, or a PZNT single crystal containing a solid solution of lead zincniobate and lead titanate. However, other various materials capable of converting electrical signals into mechanical vibration than the aforementioned materials may be used as an example of the piezoelectric material constituting the piezoelectric layer 3.

The piezoelectric layer 3 may have a single-layer structure or a multi-layer structure. Generally, a piezoelectric layer of a multi-layer structure can acquire excellent sensitivity, high energy efficiency, and a smooth spectrum since it is easy to adjust impedance and a voltage. However, any other structure for improving the performance of the piezoelectric layer 3 may be applied to the piezoelectric layer 3.

The backing layer 4 may be positioned below the piezoelectric layer 3 to absorb ultrasonic waves generated from the piezoelectric layer 3 and transmitted backward, thereby blocking ultrasonic waves from being transmitted to the back of the piezoelectric layer 3. As a result, the backing layer 4 can prevent image distortion. The backing layer 4 may be fabricated as a multi-layer structure in order to effectively attenuate or block ultrasonic waves. However, the backing layer 4 may have any other structure that can effectively attenuate or block ultrasonic waves.

The matching layer 2 may be disposed on the piezoelectric layer 3. The matching layer 2 may reduce a difference in acoustic impedances between the piezoelectric layer 3 and an object to match acoustic impedance of the piezoelectric layer 3 with acoustic impedance of the object so that ultrasonic waves generated from the piezoelectric layer 3 can be efficiently transferred to the object. In order to efficiently transfer ultrasonic waves to the object, the matching layer 2 may be configured to have, as its acoustic impedance value, a median value of an acoustic impedance value of the piezoelectric layer 3 and an acoustic impedance value of the object.

The matching layer 2 may be formed with glass or resin. However, the matching layer 2 may be formed with any other material that can match acoustic impedance of the piezoelectric layer 3 with acoustic impedance of the object.

Also, the matching layer 2 may be fabricated as a multi-layer structure so that acoustic impedance can change gradually from the piezoelectric layer 3 toward the object, and in this case, a plurality of layers constituting the matching layer 2 may be formed with different materials. However, the matching layer 2 may be fabricated as any other structure of which acoustic impedance can change gradually.

Meanwhile, the piezoelectric layer 3 and the matching layer 2 may be machined in a matrix form of a 2Dimensional (2D) array by a dicing process, or may be machined in the form of a 1Dimensional (1D) array.

The protection layer 5 may be configured to cover the upper surface of the matching layer 2 and parts of the lateral surfaces of the acoustic module 100. The protection layer 5 may be a chemical shield formed by coating or depositing a conductive material on the surface of a film having excess moisture tolerance and chemical resistance in order to protect internal components from water and chemicals for disinfection. The chemical shield may be formed by using a polymer film to form a parylene-coating on the upper surface of the matching layer 2 and the parts of the lateral surfaces of the acoustic module 100. Alternatively, the chemical shield may be formed by applying sputtering on a polymer film.

Also, the protection layer 5 may be a Radio Frequency (RF) shield to prevent high-frequency components generated by the piezoelectric layer 3 from leaking out, and to block high-frequency signals from the outside. However, the protection layer 5 may have any other structure that can intercept high-frequency components.

The lens layer 6 may be configured to cover the upper and lateral surfaces of the protection layer 5. The lens layer 6 may be formed with a low attenuation material to prevent ultrasonic signals generated from the piezoelectric layer 3 from attenuating. For example, the lens layer 6 may be formed with low viscosity epoxy resin such as DER322, or epoxy such as DEH24. However, the lens layer 6 may be formed with any other material that can prevent ultrasonic signals from attenuating. As such, by fabricating the lens layer 6 with a low attenuation material, sensitivity of ultrasonic signals may be improved.

Also, by covering parts of the lateral surfaces of the acoustic module 100, that is, parts of the kerfs of the acoustic module 100 with the lens layer 6, crosstalk may be reduced.

Hereinafter, the structures of steps, polarization areas, and first and second electrodes of a piezoelectric layer according to an embodiment of the present disclosure will be described with reference to FIGS. 2A and 2B.

Figure 2A:
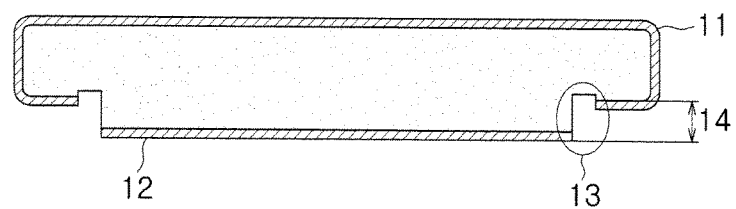
FIG. 2A is a cross-sectional view of a piezoelectric layer according to an embodiment of the present disclosure.
Figure 2B:
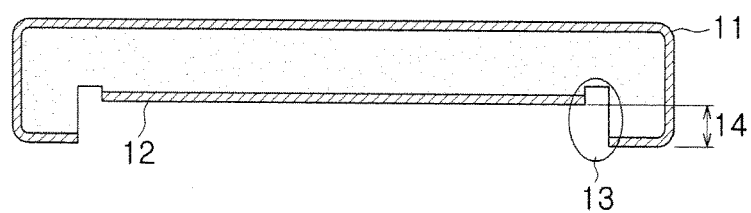
FIG. 2B is a cross-sectional view of a piezoelectric layer according to another embodiment of the present disclosure.

FIG. 2A is a cross-sectional view of a piezoelectric layer according to an embodiment of the present disclosure, and FIG. 2B is a cross-sectional view of a piezoelectric layer according to another embodiment of the present disclosure.

Referring to FIGS. 2A and 2B, a piezoelectric layer 3 may include steps 14, a first electrode 11, a second electrode 12, and polarization areas 13.

The width of the upper part of the piezoelectric layer 3 may be wider than that of the lower part of the piezoelectric layer 3. The width of the piezoelectric layer 3 may be decided according to ultrasonic waves to be generated and the performance of the ultrasonic diagnostic apparatus 1.

Also, the piezoelectric layer 3 may protrude at the center portion of the lower part, as shown in FIG. 2A, or at edge portions of the lower part, as shown in FIG. 2B. However, the piezoelectric layer 3 may be formed in any other shape that can form steps in the lower part.

Also, in the lower part of the piezoelectric layer 3, both edge portions of the piezoelectric layer 3 except for the second electrode 12 may have a less influence on ultrasonic waves generated from the piezoelectric layer 3. Accordingly, by forming the steps 14 in space located in both edge portions of the lower part of the piezoelectric layer 3 so that the matching layer 2, a flexible printed circuit board, the backing layer 4, and the piezoelectric layer 3 are structurally integrated, high accuracy and high yield can be ensured in a manufacturing process of connecting the matching layer 2, the flexible printed circuit board, the backing layer 4, and the piezoelectric layer 3 to each other.

Also, the length of the step 14 of the piezoelectric layer 3 may be arbitrarily decided in the space of the piezoelectric layer 3 that is a range in which the piezoelectric performance of the piezoelectric layer 3 is not degraded. For example, the length of the step 14 of the piezoelectric layer 3 may be decided to correspond to a thickness of a flexible printed circuit board to which the piezoelectric layer 3 is to be connected. However, the length of the step 14 may be decided to an arbitrary length that can facilitate manufacturing of the ultrasonic diagnostic apparatus 1 in a range in which the piezoelectric performance of the piezoelectric layer 3 is not degraded.

Also, the steps 14 of the piezoelectric layer 3 may be formed by bonding another ceramic using epoxy or by etching using laser. Also, the steps 14 may be formed through a dicing process, a grinding process, or an etching process. However, the steps 14 of the piezoelectric layer 3 may be formed by any other method than the aforementioned methods.

Also, a thickness of the piezoelectric layer 3 may be decided in consideration of an ultrasonic wave frequency that is used by the ultrasonic diagnostic apparatus 1. Generally, an ultrasonic wave frequency increases at a thinner thickness of the piezoelectric layer 3. Accordingly, the piezoelectric layer 3 having a thick thickness may be used in order to use ultrasonic waves of a low frequency, and the piezoelectric layer 3 having a thin thickness may be used in order to use ultrasonic waves of a high frequency.

The piezoelectric layer 3 may include the first electrode 11 and the second electrode 12. The first electrode 11 of the piezoelectric layer 3 may be formed to cover the entire upper surface of the piezoelectric layer 3 and the edge portions of the lower surface of the piezoelectric layer 3. Also, the second electrode 12 of the piezoelectric layer 3 may be formed on the lower surface of the piezoelectric layer 3 to extend to the polarization areas 13 adjacent to the first electrode 11. The first and second electrodes 11 and 12 of the piezoelectric layer 3 may be formed with a high conductivity material, and may be formed with a flexible material in order to be resistant against piezoelectric vibration.

Each polarization area 13 may be used to electrically separate the first electrode 11 of the piezoelectric layer 3 from the second electrode 12 of the piezoelectric layer 3. Accordingly, the polarization area 13 may be located between the first electrode 11 of the piezoelectric layer 3 and the second electrode 12 of the piezoelectric layer 3.

The polarization area 13 may be formed in the shape of a groove, or in the shape of a protrusion, or in the shape of a plane, between the first electrode 11 of the piezoelectric layer 3 and the second electrode 12 of the piezoelectric layer 3, as shown in FIGS. 2A and 2B. However, the polarization area 13 may be formed in any other shape that can separate the first electrode 11 of the piezoelectric layer 3 from the second electrode 12 of the piezoelectric layer 3.

Also, the polarization area 13 may be formed with a low conductivity material in order to electrically separate the first electrode 11 of the piezoelectric layer 3 from the second electrode 12 of the piezoelectric layer 3. However, the polarization area 13 may be formed with any other material that can electrically separate the first electrode 11 of the piezoelectric layer 3 from the second electrode 12 of the piezoelectric layer 3.

Hereinafter, an ultrasonic diagnostic apparatus having an integrated flexible printed circuit board, according to an embodiment of the present disclosure, will be described with reference to FIGS. 3A to 5.

Figure 3A:
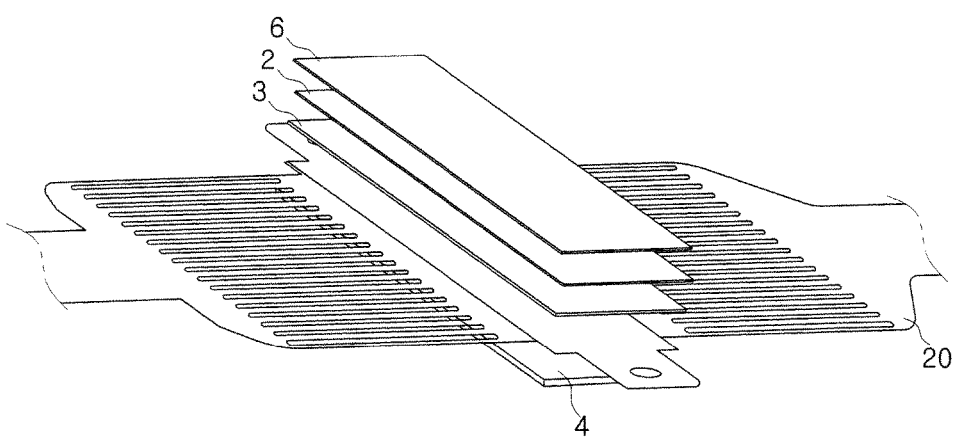
FIG. 3A is a perspective view of an ultrasonic diagnosis apparatus according to an embodiment of the present disclosure.
Figure 3B:
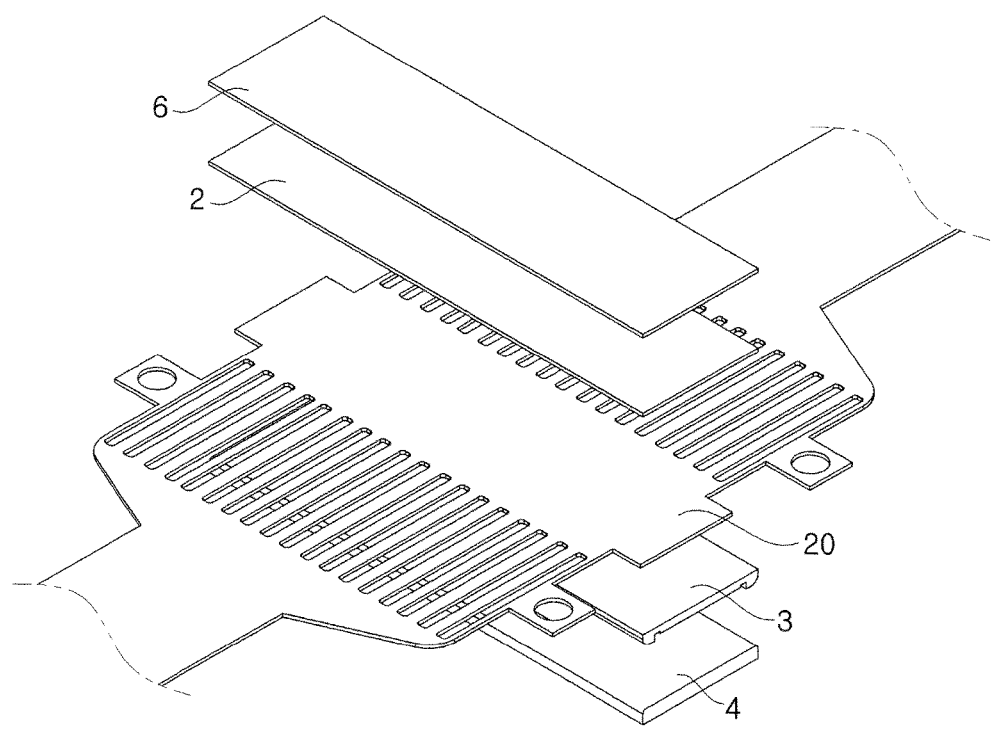
FIG. 3B is a perspective view of an ultrasonic diagnosis apparatus according to another embodiment of the present disclosure.
Figure 4A:
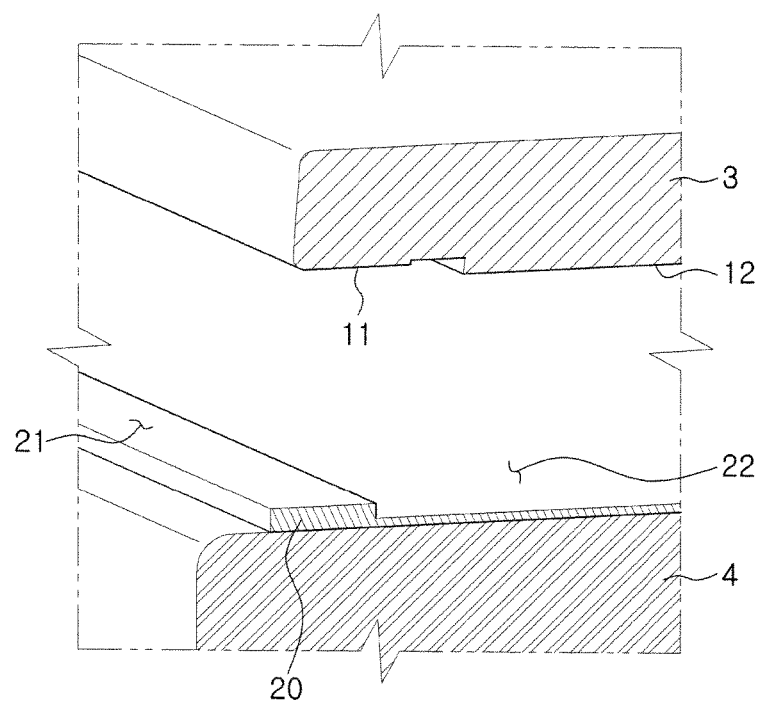
FIG. 4A is a perspective view showing a piezoelectric layer according to an embodiment of the present disclosure, an integrated flexible printed circuit board, and a backing layer.
Figure 4B:
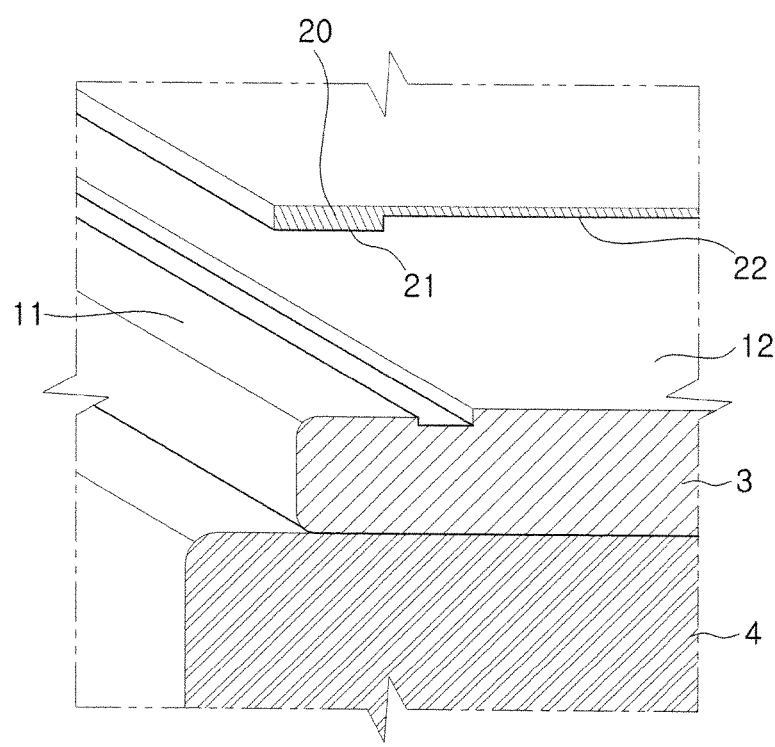
FIG. 4B is a perspective view showing a piezoelectric layer according to another embodiment of the present disclosure, an integrated flexible printed circuit board, and a backing layer.

FIG. 3A is a perspective view of an ultrasonic diagnosis apparatus according to an embodiment of the present disclosure, FIG. 3B is a perspective view of an ultrasonic diagnosis apparatus according to another embodiment of the present disclosure, FIG. 4A is a perspective view showing a piezoelectric layer according to an embodiment of the present disclosure, an integrated flexible printed circuit board, and a backing layer, FIG. 4B is a perspective view showing a piezoelectric layer according to another embodiment of the present disclosure, an integrated flexible printed circuit board, and a backing layer, and FIG. 5 is a top view of an integrated flexible printed circuit board according to an embodiment of the present disclosure.

Referring to FIG. 3A, an ultrasonic diagnostic apparatus 1 may include a lens layer 6, a matching layer 2, a piezoelectric layer 3, a backing layer 4, and an integrated flexible printed circuit board 20.

In detail, the lens layer 6 may prevent ultrasonic signals generated from the piezoelectric layer 3 from attenuating, and the matching layer 2 may reduce a difference in acoustic impedance between the piezoelectric layer 3 and an object to match acoustic impedance of the piezoelectric layer 3 with acoustic impedance of the object so that ultrasonic waves generated from the piezoelectric layer 3 can be efficiently transferred to the object. The piezoelectric layer 3 may convert electricity energy into mechanical vibration energy and mechanical vibration energy into electricity, and the backing layer 4 may absorb ultrasonic waves generated from the piezoelectric layer 3 and transmitted backward to thereby block ultrasonic waves from being transmitted to the back of the piezoelectric layer 3.

Also, the integrated flexible printed circuit board 20 may be a single flexible printed circuit board (FPCB) that is electrically connected to the piezoelectric layer 3. The flexible printed circuit board 20 may be a circuit board fabricated by attaching a flexible copper film on a thin insulating film having a thickness of 10 μm. Accordingly, the flexible printed circuit board 20 may be fabricated with a heat-resistant plastic film, such as polyester (PET) or polyimide (PI), which is a flexible material, to have flexibility allowing bending, overlapping, folding, rolling, twisting, and the like, unlike a rigid printed circuit board made of a rigid material, thereby facilitating effective use of space and 3Dimensional (3D) wiring.

As shown in FIG. 4A, the piezoelectric layer 3 may be connected to the flexible printed circuit board 20 by coupling steps as female and male to each other. The piezoelectric layer 3 may protrude at the center portion of the lower part, or at the edge portions of the lower part. Also, the first electrode 11 of the piezoelectric layer 3 may be formed on both edge portions of the lower part, and the second electrode 12 of the piezoelectric layer 3 may be formed on the center portion of the lower part. Also, the integrated flexible printed circuit board 20 may protrude or be caved in at both edge portions of the upper part. Also, the first electrode 21 of the integrated flexible printed circuit board 20 may be formed on both edge portions of the upper part of the integrated flexible printed circuit board 20, and the second electrode 22 of the integrated flexible printed circuit board 20 may be formed on the center portion of the upper part of the integrated flexible printed circuit board 20. Accordingly, the piezoelectric layer 3 can be tightly coupled with the integrated flexible printed circuit board 20 through the steps that are coupled with each other as female and male. As a result, the first electrode 11 of the piezoelectric layer 3 may be electrically connected to the first electrode 21 of the integrated flexible printed circuit board 20, and the second electrode 12 of the piezoelectric layer 3 may be electrically connected to the second electrode 22 of the integrated flexible printed circuit board 20.

Also, the piezoelectric layer 3 may be connected to the integrated flexible printed circuit board 20, and the lower part of the integrated flexible printed circuit board 20 may be connected to the upper part of the backing layer 4.

As shown in FIG. 4B, the piezoelectric layer 3 may be connected to the integrated flexible printed circuit board 20 such that steps correspond, as female and male, to each other. More specifically, the piezoelectric layer 3 may protrude at the center portion of the upper part, or at edge portions of the upper part. Also, a first electrode 11 of the piezoelectric layer 3 may be formed at both edge portions of the upper part, and a second electrode 12 of the piezoelectric layer 3 may be formed on the center portion of the upper part. The integrated flexible printed circuit board 20 may protrude or be caved in at both edge portions of the lower part. Also, a first electrode 21 of the integrated flexible printed circuit board 20 may be formed at both edge portions of the lower part, and a second electrode 22 of the integrated flexible printed circuit board 20 may be formed on the center portion of the lower part. Accordingly, the piezoelectric layer 3 may be tightly coupled with the integrated flexible printed circuit board 20 along steps that are coupled with each other as female and male. Therefore, the first electrode 11 of the piezoelectric layer 3 may be electrically connected to the first electrode 21 of the integrated flexible printed circuit board 20, and the second electrode 12 of the piezoelectric layer 3 may be electrically connected to the second electrode 22 of the integrated flexible printed circuit board 20.

Also, the piezoelectric layer 3 may be coupled with the integrated flexible printed circuit board 20, and the lower part of the piezoelectric layer 3 may be coupled with the upper part of the backing layer 4.

If the first electrodes 11 and 22 of the piezoelectric layer 3 and the integrated printed circuit board 20 are electrically connected to each other, and the second electrodes 12 and 22 of the piezoelectric layer 3 and the integrated printed circuit board 20 are electrically connected to each other, the first electrode 21 of the integrated printed circuit board 20 may be connected to the ground, and the second electrode 22 of the integrated printed circuit board 20 may be connected to an ultrasonic wave generator. Also, the first electrode 11 of the piezoelectric layer 3 may be connected to the ground, and the second electrode 12 of the piezoelectric layer 3 may be connected to the ultrasonic wave generator. Accordingly, a ground signal and an ultrasonic signal may be respectively transferred to the first electrode 11 and the second electrode 12 of the piezoelectric layer 3 through connection parts 23 of the flexible printed circuit board 20, so that the piezoelectric layer 3 can generate desired ultrasonic waves.

Hereinafter, an ultrasonic diagnostic apparatus having separated flexible printed circuit boards will be described with reference to FIGS. 6A to 8.

Figure 6A:
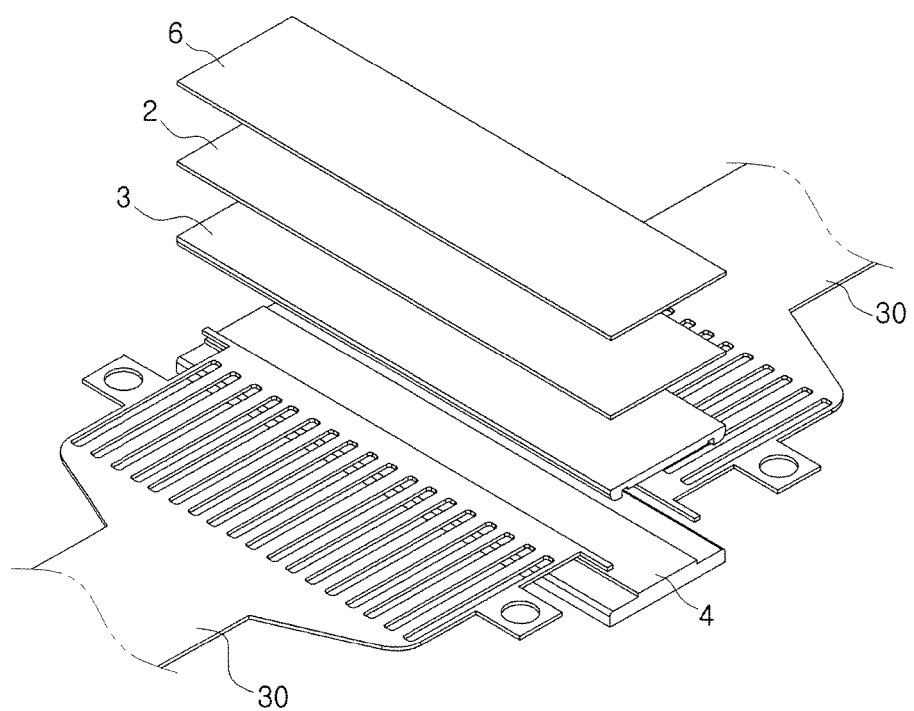
FIG. 6A is a perspective view of an ultrasonic diagnostic apparatus according to an embodiment of the present disclosure.
Figure 6B:
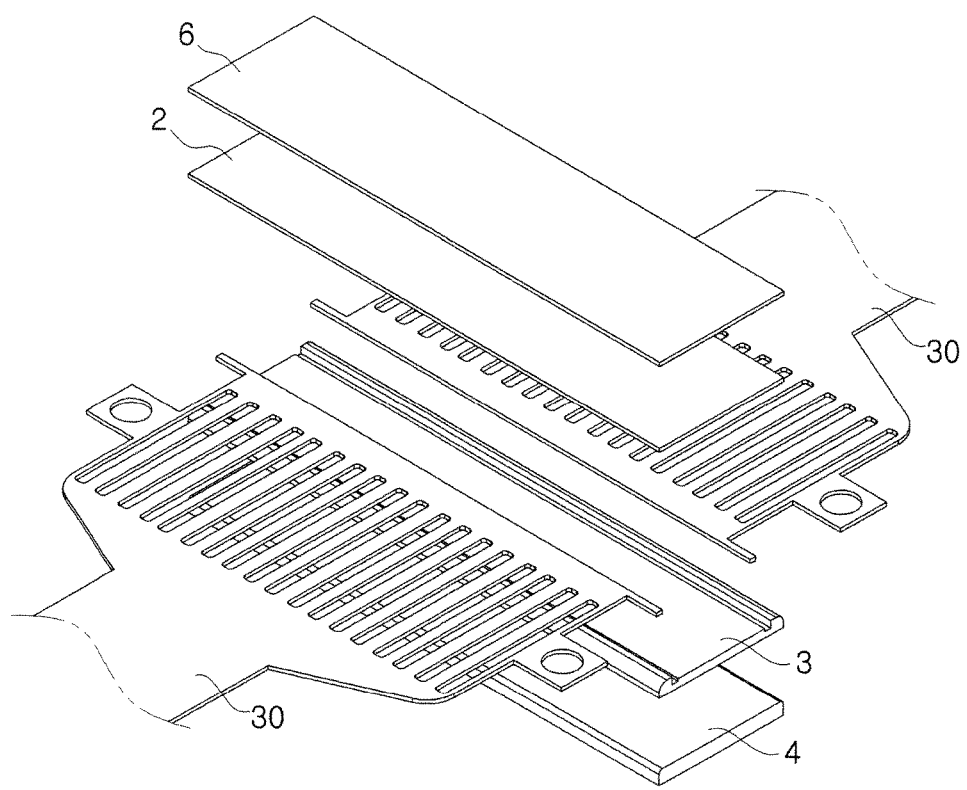
FIG. 6B is a perspective view of an ultrasonic diagnostic apparatus according to another embodiment of the present disclosure.
Figure 7A:
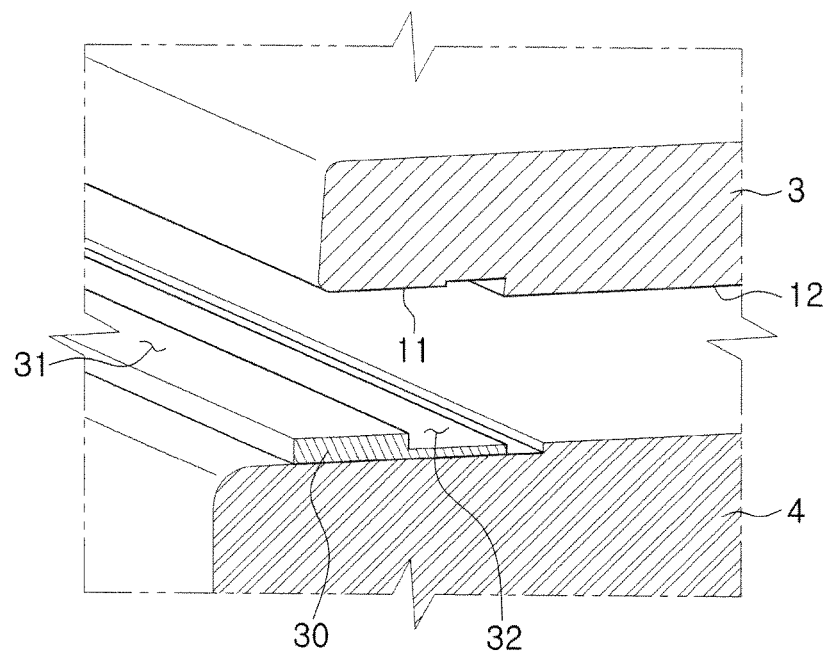
FIG. 7A is a perspective view showing a piezoelectric layer according to an embodiment of the present disclosure, a separated flexible printed circuit board, and a backing layer.
Figure 7B:
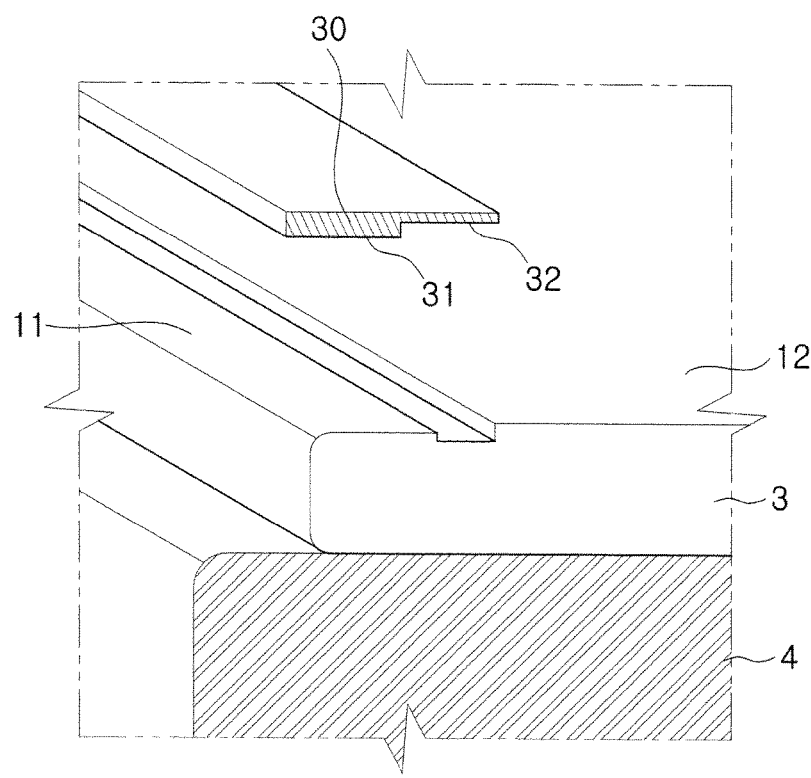
FIG. 7B is a perspective view showing a piezoelectric layer according to another embodiment of the present disclosure, a separated flexible printed circuit board, and a backing layer.
Figure 8:
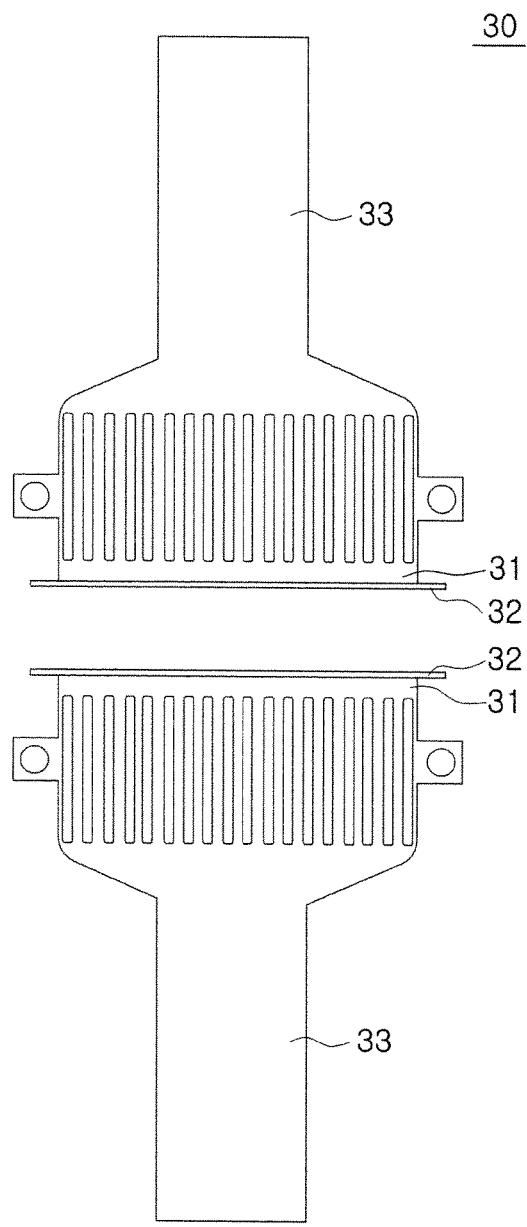
FIG. 8 is a top view of separated flexible printed circuit boards according to an embodiment of the present disclosure.

FIG. 6A is a perspective view of an ultrasonic diagnostic apparatus according to an embodiment of the present disclosure, FIG. 6B is a perspective view of an ultrasonic diagnostic apparatus according to another embodiment of the present disclosure, FIG. 7A is a perspective view showing a piezoelectric layer according to an embodiment of the present disclosure, a separated flexible printed circuit board, and a backing layer, FIG. 7B is a perspective view showing a piezoelectric layer according to another embodiment of the present disclosure, a separated flexible printed circuit board, and a backing layer, and FIG. 8 is a top view of separated flexible printed circuit boards according to an embodiment of the present disclosure.

Referring to FIG. 6A, an ultrasonic diagnostic apparatus 1 may include a lens layer 6, a matching layer 2, a piezoelectric layer 3, a backing layer 4, and separated flexible printed circuit boards 30.

The lens layer 6 may prevent ultrasonic signals generated from the piezoelectric layer 3 from attenuating, and the matching layer 2 may reduce a difference in acoustic impedance between the piezoelectric layer 3 and an object to match acoustic impedance of the piezoelectric layer 3 with acoustic impedance of the object so that ultrasonic waves generated from the piezoelectric layer 3 can be efficiently transferred to the object. Also, the piezoelectric layer 3 may convert electricity energy into mechanical vibration energy and mechanical vibration energy into electricity energy. The backing layer 4 may absorb ultrasonic waves generated from the piezoelectric layer 3 and transferred backward to thereby block ultrasonic waves from being transmitted to the back of the piezoelectric layer 3.

The separated flexible printed circuit boards 30 may be a single flexible printed circuit board (FPCB) that is electrically connected to the piezoelectric layer 3. The separated printed circuit boards 30 may be fabricated with the same material as or a different material from the integrated flexible printed circuit board 30 described above.

As shown in FIG. 7A, the piezoelectric layer 3 may be coupled with two separated printed circuit boards 30 by coupling steps as female and male with each other. The piezoelectric layer 3 may protrude at the center portion of the lower part, as shown in FIG. 2A, or at both edge portions of the lower part, as shown in FIG. 2B. Also, a first electrode 11 of the piezoelectric layer 3 may be formed on both edge portions of the lower part of the piezoelectric layer 3, and a second electrode 12 of the piezoelectric layer 3 may be formed on the center portion of the lower part of the piezoelectric layer 3. Each separated flexible printed circuit board 30 may protrude or be caved in at one edge portion of the upper part. Also, a first electrode 31 of the separated flexible printed circuit board 30 may be formed on one edge portion of the upper part of the separated flexible printed circuit board 30, and a second electrode 32 of the separated flexible printed circuit board 30 may be formed on the center portion of the upper part of the separated flexible printed circuit board 30. Accordingly, when the piezoelectric layer 3 is coupled with the separated flexible printed circuit boards 30, the piezoelectric layer 3 can be tightly coupled with the separated flexible printed circuit boards 30 through the steps that are coupled with each other as female and male. As a result, the first electrode 11 of the piezoelectric layer 3 may be electrically connected to the first electrodes 31 of the separated flexible printed circuit boards 30, and the second electrode 12 of the piezoelectric layer 3 may be electrically connected to the second electrodes 32 of the separated flexible printed circuit boards 30.

Also, the piezoelectric layer 3 may be coupled with the separated flexible printed circuit boards 30, and the lower parts of the separated flexible printed circuit boards 30 may be coupled with the upper part of the backing layer 4.

As shown in FIG. 7B, the piezoelectric layer 3 may be coupled with the two separated flexible printed circuit boards 30 by coupling the corresponding steps as female and male with each other. The piezoelectric layer 3 may protrude at the center portion of the upper part, or at both edge portions of the upper part. Also, the first electrode 11 of the piezoelectric layer 3 may be formed on both edge portions of the upper part of the piezoelectric layer 3, and the second electrode 12 of the piezoelectric layer 3 may be formed on the center portion of the upper part of the piezoelectric layer 3. Also, each separated flexible printed circuit board 30 may protrude or be caved in at one edge portion of the lower part. Also, the first electrode 31 of the separated flexible printed circuit board 30 may be formed on one edge portion of the lower part of the separated flexible printed circuit board 30, and the second electrode 32 of the separated flexible printed circuit board 30 may be formed on the center portion of the lower part of the separated flexible printed circuit board 30. Accordingly, the piezoelectric layer 3 can be tightly coupled with the separated flexible printed circuit boards 30 through the steps that are coupled with each other as female and male. As a result, the first electrode 11 of the piezoelectric layer 3 may be electrically connected to the first electrodes 31 of the separated flexible printed circuit boards 30, and the second electrode 12 of the piezoelectric layer 3 may be electrically connected to the second electrodes 32 of the separated flexible printed circuit boards 30.

Also, the piezoelectric layer 3 may be coupled with the separated flexible printed circuit boards 30, and the lower part of the piezoelectric layer 3 may be coupled with the upper part of the backing layer 4.

If the first electrodes 11 and 32 of the piezoelectric layer 3 and the separated printed circuit boards 30 are electrically connected to each other, and the second electrodes 12 and 32 of the piezoelectric layer 3 and the separated printed circuit boards 30 are electrically connected to each other, the first electrodes 31 of the separated printed circuit boards 30 may be connected to the ground, and the second electrodes 32 of the separated printed circuit boards 30 may be connected to the ultrasonic wave generator. Also, the first electrode 11 of the piezoelectric layer 3 may be connected to the ground, and the second electrode 12 of the piezoelectric layer 3 may be connected to the ultrasonic wave generator. Accordingly, a ground signal and an ultrasonic signal may be respectively transferred to the first electrode 11 and the second electrode 12 of the piezoelectric layer 3 through connection parts 33 of the flexible printed circuit boards 20, so that the piezoelectric layer 3 can generate desired ultrasonic waves.

Hereinafter, a piezoelectric layer configured with ceramic composites consisting of ceramic and epoxy, according to an embodiment of the present disclosure, will be described with reference to FIGS. 9A to 9C.

Figure 9A:
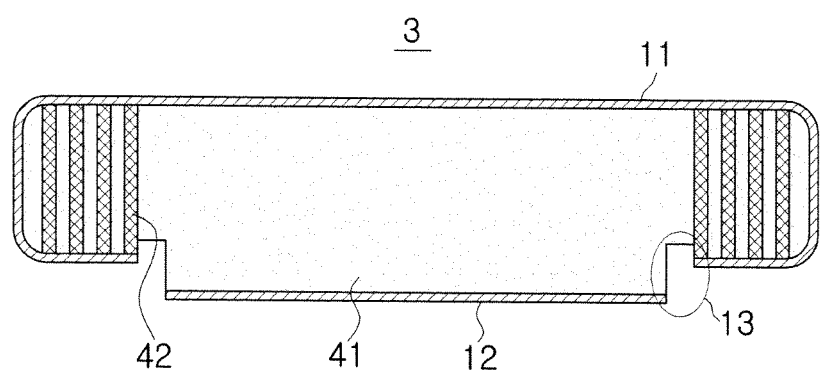
FIG. 9A is a cross-sectional view of a piezoelectric layer with both edge portions configured with ceramic composites, according to an embodiment of the present disclosure.
Figure 9B:
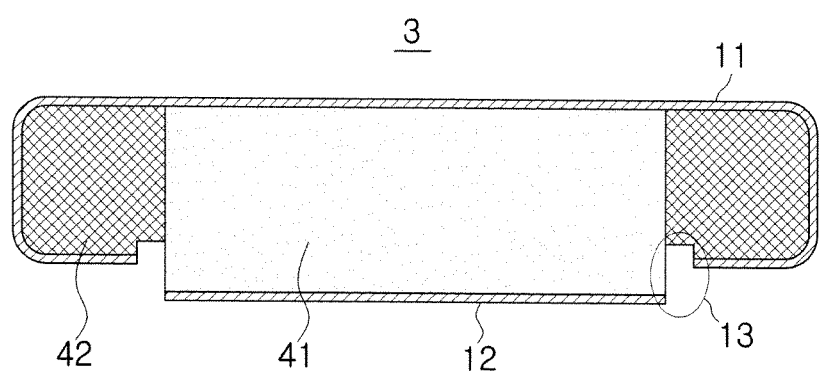
FIG. 9B is a cross-sectional view of a ceramic composites piezoelectric layer whose both edge portions are configured with epoxy and whose center portion is configured with a ceramic, according to an embodiment of the present disclosure.
Figure 9C:
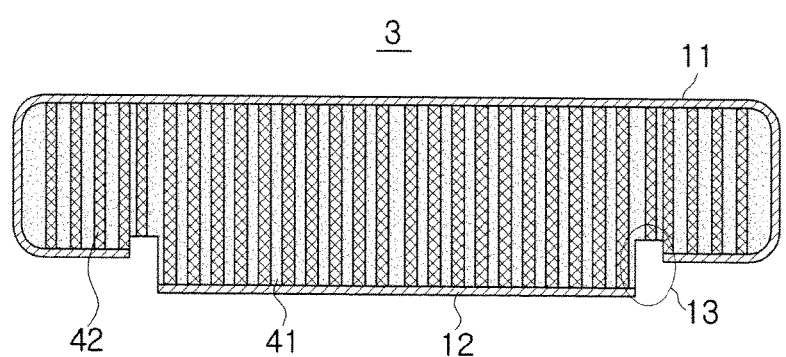
FIG. 9C is a cross-sectional view of a piezoelectric layer configured with ceramic composites, according to an embodiment of the present disclosure.

FIG. 9A is a cross-sectional view of a piezoelectric layer with both edge portions configured with ceramic composites, according to an embodiment of the present disclosure, FIG. 9B is a cross-sectional view of a ceramic composites piezoelectric layer whose both edge portions are configured with epoxy and whose center portion is configured with ceramic, according to an embodiment of the present disclosure, and FIG. 9C is a cross-sectional view of a piezoelectric layer configured with ceramic composites, according to an embodiment of the present disclosure.

Ceramic composites may be configured by alternately arranging epoxy layers and ceramic layers, or by forming a predetermined portion with epoxy and the remaining portion with ceramic.

A method of alternately arranging epoxy layers 42 and ceramic layers 41 vertically to the upper and lower surfaces of the piezoelectric layer 3 may be forming notches in a ceramic layer to inject epoxy between the ceramic layer through a dicing process, or directly bonding a plurality of ceramic layers with epoxy. However, the method of alternately arranging the epoxy layers 42 and the ceramic layers 41 vertically to the upper and lower surfaces of the piezoelectric layer 3 is not limited to the above-described methods.

The piezoelectric layer 3 may be configured with ceramic composites at both edges portions, as shown in FIG. 9A, or the piezoelectric layer 3 may be configured with epoxy 42 at both edge portions and with ceramic 41 at the center portion, as shown in FIG. 9B. Also, the entire of the piezoelectric layer 3 may be configured with ceramic composites consisting of ceramic layers 41 and epoxy layers 42, as shown in FIG. 9C.

However, the material of the piezoelectric layer 3 is not limited to ceramic composites. That is, the piezoelectric layer 3 may be formed with any other material or in any other shape, as long as the piezoelectric performance of the piezoelectric layer 3 can be maintained at a predetermined level.

Hereinafter, a method of manufacturing an ultrasonic diagnostic apparatus, according to an embodiment of the present disclosure, will be described with reference to FIGS. 10A and 10B.

FIG. 10A is a flowchart sequentially illustrating a method of manufacturing an ultrasonic diagnostic apparatus, according to an embodiment of the present disclosure.

First, a dicing process may be used to fabricate a piezoelectric substance with ceramic composites configured by alternately arranging ceramic layers and epoxy layers in parallel and vertically to the upper and lower surfaces of the piezoelectric substance, in operation S10. Then, steps may be formed in the piezoelectric substance, so that a piezoelectric layer that can be used in an ultrasonic diagnostic apparatus may be fabricated, in operation S20.

Successively, a backing layer may be prepared, in operation S30, a flexible printed circuit board may be placed on the backing layer, in operation S40, and the piezoelectric layer may be placed on the flexible printed circuit board, in operation S50.

Thereafter, the flexible printed circuit board may be tightly coupled with the piezoelectric layer such that a first electrode of the flexible printed circuit board is electrically connected to a first electrode of the piezoelectric layer, and a second electrode of the flexible printed circuit board is electrically connected to a second electrode of the piezoelectric layer, in operation S60. Then, a matching layer may be placed on the piezoelectric layer, thereby completing an ultrasonic diagnostic apparatus, in operation S70.

FIG. 10B is a flowchart illustrating a method of manufacturing an ultrasonic diagnostic apparatus, according to another embodiment of the present disclosure.

First, a dicing process may be used to fabricate a piezoelectric substance with ceramic composites configured by alternately arranging ceramic layers and epoxy layers in parallel and vertically to the upper and lower surfaces of the piezoelectric substance, in operation S110. Then, steps may be formed in the piezoelectric substance, so that a piezoelectric layer that can be used in an ultrasonic diagnostic apparatus may be fabricated, in operation S120. Successively, a backing layer may be prepared, in operation S130, the piezoelectric layer may be placed on the backing layer, in operation S140, and a flexible printed circuit board may be placed on the piezoelectric layer, in operation S150.

Thereafter, the flexible printed circuit board may be tightly coupled with the piezoelectric layer such that a first electrode of the flexible printed circuit board is electrically connected to a first electrode of the piezoelectric layer, and a second electrode of the flexible printed circuit board is electrically connected to a second electrode of the piezoelectric layer, in operation S160. Then, a matching layer may be placed on the flexible printed circuit board, in operation S170, thereby completing an ultrasonic diagnostic apparatus.

According to the ultrasonic diagnostic apparatus and the manufacturing method thereof, by configuring the ultrasonic diagnostic apparatus with a piezoelectric layer having steps, it is possible to improve yield while maintaining the performance of the ultrasonic diagnostic apparatus.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasonic diagnostic apparatus comprising:
   a matching layer;
   a piezoelectric layer disposed below the matching layer, and having steps with respect to polarization areas;
   a backing layer disposed below the piezoelectric layer; and
   a flexible printed circuit board having at least one step protruding from at least one edge portion of an upper surface or a lower surface of the flexible printed circuit board in a longitudinal direction, and being connected to the piezoelectric layer, where the steps of the piezoelectric layer and the at least one step of the flexible printed circuit correspond to each other,
   wherein the steps of the piezoelectric layer protrude from one of a middle portion of a lower surface of the piezoelectric layer, edge portions of the lower surface of the piezoelectric layer, a middle portion of an upper surface of the piezoelectric layer, or edge portions of the upper surface of the piezoelectric layer.

2. The ultrasonic diagnostic apparatus of claim 1, wherein the flexible printed circuit board is disposed on the backing layer and has steps protruding from both edge portions of the upper surface of the flexible printed circuit board in the longitudinal direction,
   wherein a first electrode and a second electrode of the piezoelectric layer, between which the steps protrude from the middle portion of the lower surface of the piezoelectric layer or from the edge portions of the lower surface of the piezoelectric layer and which are separated from each other by the polarization areas, are respectively connected to a first electrode and a second electrode of the flexible printed circuit board, the piezoelectric layer disposed below the matching layer and on the flexible printed circuit board.

3. The ultrasonic diagnostic apparatus of claim 1, wherein the flexible printed circuit board is disposed below the matching layer and has steps protruding from at both edge portions of the lower surface of the flexible printed circuit board in the longitudinal direction, wherein a first electrode and a second electrode of the piezoelectric layer, between which the steps protrude from the middle portion of the upper surface of the piezoelectric layer or from the edge portions of the upper surface of the piezoelectric layer and which are separated from each other by the polarization areas, are respectively connected to a first electrode and a second electrode of the flexible printed circuit board, the piezoelectric layer disposed below the flexible printed circuit board and on the backing layer.

4. The ultrasonic diagnostic apparatus of claim 1, wherein the flexible printed circuit board is provided with a plurality of flexible printed circuit boards disposed on the backing layer, each flexible printed circuit board having a step protruding from one edge portion of an upper surface of the plurality of flexible printed circuit boards in the longitudinal direction, wherein a first electrode and a second electrode of the piezoelectric layer, between which the steps protrude from the middle portion of the lower surface of the piezoelectric layer or from the edge portions of the lower surface of the piezoelectric layer and which are separated from each other by the polarization areas, are respectively connected to first electrodes and second electrodes of the flexible printed circuit boards, the piezoelectric layer disposed below the matching layer and on the flexible printed circuit boards.

5. The ultrasonic diagnostic apparatus of claim 1, wherein the flexible printed circuit board is provided with a plurality of flexible printed circuit boards disposed below the matching layer, each flexible printed circuit board having a step protruding from one edge portion of a lower surface of the plurality of flexible printed circuit boards in the longitudinal direction, wherein a first electrode and a second electrode of the piezoelectric layer, between which the steps protrude from the middle portion of the upper surface of the piezoelectric layer or from the edge portions of the upper surface of the piezoelectric layer and which are separated from each other by the polarization areas, are respectively connected to first electrodes and second electrodes of the flexible printed circuit boards, the piezoelectric layer disposed below the flexible printed circuit boards and on the backing layer.

6. The ultrasonic diagnostic apparatus of claim 2, wherein the first electrode of the flexible printed circuit board is connected to a ground, and the second electrode of the flexible printed circuit board is connected to an ultrasonic wave generator.

7. The ultrasonic diagnostic apparatus of claim 2, wherein the first electrode of the flexible printed circuit board is connected to an ultrasonic wave generator, and the second electrode of the flexible printed circuit board is connected to a ground.

8. The ultrasonic diagnostic apparatus of claim 2, wherein each step of the piezoelectric layer corresponds to a thickness of the flexible printed circuit board.

9. The ultrasonic diagnostic apparatus of claim 1, wherein the piezoelectric layer is configured with ceramic composites.

10. The ultrasonic diagnostic apparatus of claim 1, wherein both edge portions of the piezoelectric layer are formed with a material that is different from a material of the center portion of the piezoelectric layer.

11. A method of manufacturing an ultrasonic diagnostic apparatus, comprising:
providing a backing layer;
placing a piezoelectric layer having steps with respect to polarization areas on the backing layer;
placing a matching layer on the piezoelectric layer; and
placing a flexible printed circuit board on or below the piezoelectric layer, the flexible printed circuit board having at least one step protruding from at least one edge portion of an upper surface or a lower surface of the flexible printed circuit board in a longitudinal direction, and being connected to the piezoelectric layer, where the steps of the piezoelectric layer and the at least one step of the flexible printed circuit correspond to each other, wherein the steps of the piezoelectric layer protrude from one of a middle portion of a lower surface of the piezoelectric layer, edge portions of the lower surface of the piezoelectric layer, a middle portion of an upper surface of the piezoelectric layer, or edge portions of the upper surface of the piezoelectric layer.

12. The method of claim 11, wherein the flexible printed circuit board has steps protruding from both edge portions of the upper surface of the flexible printed circuit board in the longitudinal direction on the backing layer, wherein the placing of the piezoelectric layer comprises placing the piezoelectric layer on the flexible printed circuit board such that a first electrode and a second electrode of the piezoelectric layer, which have the steps protruding from the middle portion of the lower surface of the piezoelectric layer or from the edge portions of the lower surface of the piezoelectric layer with respect to the polarization areas, are respectively connected to a first electrode and a second electrode of the flexible printed circuit boards.

13. The method of claim 11, wherein the flexible printed circuit board has steps protruding from both edge portions of the lower surface of the flexible printed circuit board in the longitudinal direction below the matching layer, wherein the placing of the piezoelectric layer comprises placing the piezoelectric layer below the flexible printed circuit board such that a first electrode and a second electrode of the piezoelectric layer, which have the steps protruding from the middle portion of the upper surface of the piezoelectric layer or from the edge portions of the upper surface of the piezoelectric layer with respect to the polarization areas, are respectively connected to a first electrode and a second electrode of the flexible printed circuit board.

14. The method of claim 12, further comprising connecting a first electrode of the flexible printed circuit board to a ground, and connecting a second electrode of the flexible printed circuit board to an ultrasonic wave generator.

15. The method of claim 12, further comprising connecting a first electrode of the flexible printed circuit board to an ultrasonic wave generator, and connecting a second electrode of the flexible printed circuit board to a ground.

16. The method of claim 12, further comprising forming the steps of the piezoelectric layer, each step corresponding to a thickness of the flexible printed circuit board.

17. The method of claim 11, further comprising forming the piezoelectric layer with ceramic composites.

18. The method of claim 11, further comprising forming the piezoelectric layer such that both edge portions of the piezoelectric layer are formed with a material that is different from a material of the center portion of the piezoelectric layer.

* * * * *